United States Patent [19]
Hughes

[11] Patent Number: 5,757,881
[45] Date of Patent: May 26, 1998

[54] REDUNDANT FIELD-DEFINING ARRAYS FOR A RADIATION SYSTEM

[75] Inventor: John H. Hughes, Martinez, Calif.

[73] Assignee: Siemens Business Communication Systems, Inc., Santa Clara, Calif.

[21] Appl. No.: 779,177

[22] Filed: Jan. 6, 1997

[51] Int. Cl.⁶ .................................................. G21K 1/04
[52] U.S. Cl. .......................... 378/65; 378/152; 250/505.1
[58] Field of Search ............................. 378/64, 65, 150, 378/152, 147, 153; 250/505.1

[56] References Cited

U.S. PATENT DOCUMENTS

| | | | |
|---|---|---|---|
| 4,140,129 | 2/1979 | Heinz et al. | 128/404 |
| 4,220,866 | 9/1980 | Taumann et al. | 250/513 |
| 4,314,158 | 2/1982 | Lucido | 250/505 |
| 4,882,741 | 11/1989 | Brown | 378/152 |
| 5,165,106 | 11/1992 | Barthelmes et al. | 250/505.1 |
| 5,166,531 | 11/1992 | Huntzinger | 378/152 X |
| 5,278,886 | 1/1994 | Kobiki et al. | 378/65 |

Primary Examiner—David P. Porta

[57] ABSTRACT

A system for applying radiation therapy includes a radiation source for emitting a radiation beam and includes redundant treatment field-defining arrays for shaping the radiation beam. The radiation beam is initially shaped by a multileaf collimator having a side-by-side arrangement of leaf pairs. The leaves are individually manipulable to define apertures between the leaves of a pair. Thus, the contour of an irregular treatment field can be precisely defined. The second field-defining array includes field-defining members that are individually connected to corresponding leaves of the multileaf collimator. Preferably, the connections are mechanical linkages and there is a one-to-one correspondence of the field-defining members and the leaves. Adjustment of a leaf simultaneously adjusts a position of a corresponding field-defining member. Also in the preferred embodiment, the second array is contained within a conically shaped housing that provides beam guidance. As a result of the shape of the housing and the redundant arrays, healthy tissue is shielded during irradiation of a patient.

16 Claims, 2 Drawing Sheets

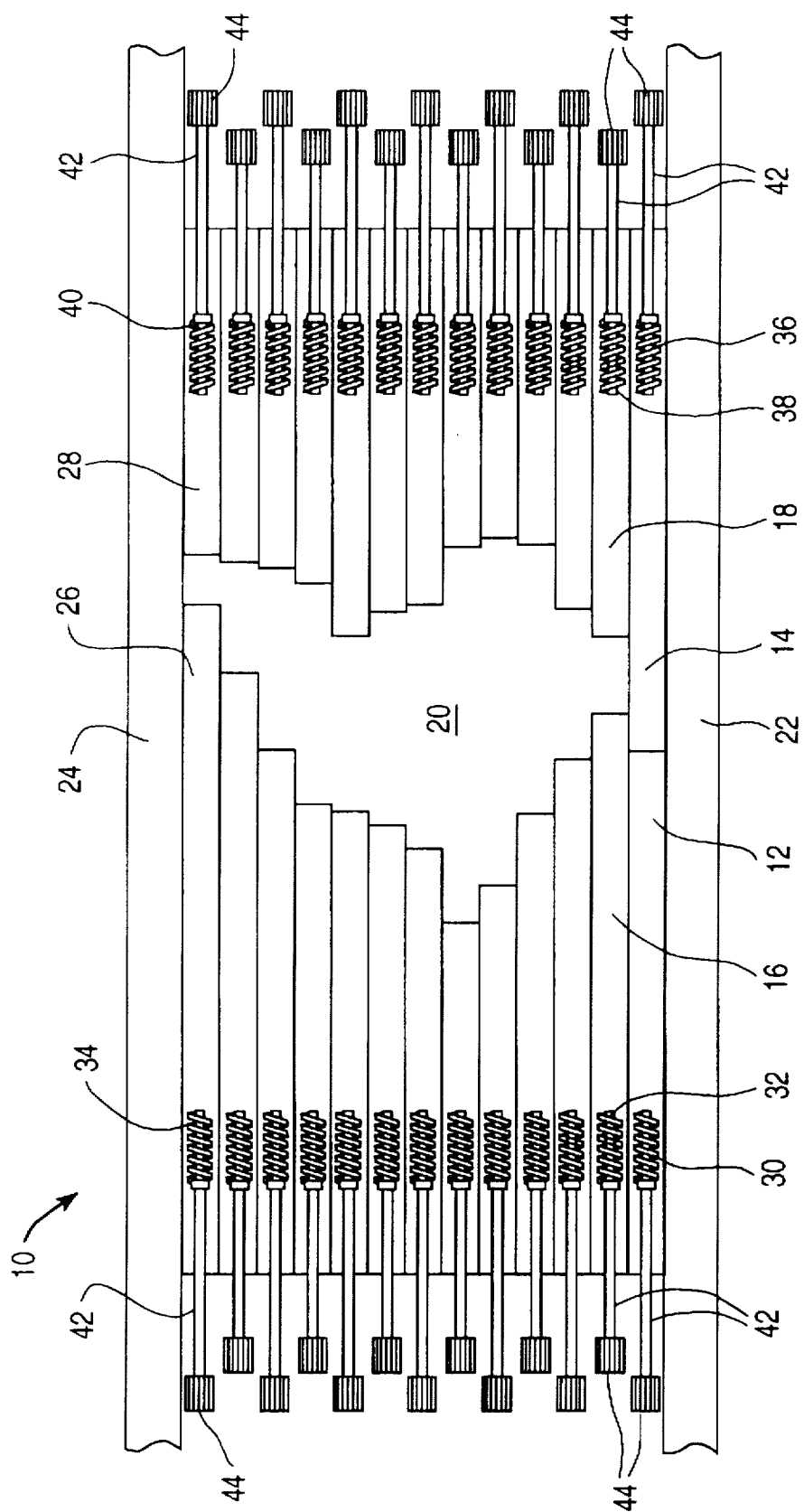
FIG_1 (PRIOR ART)

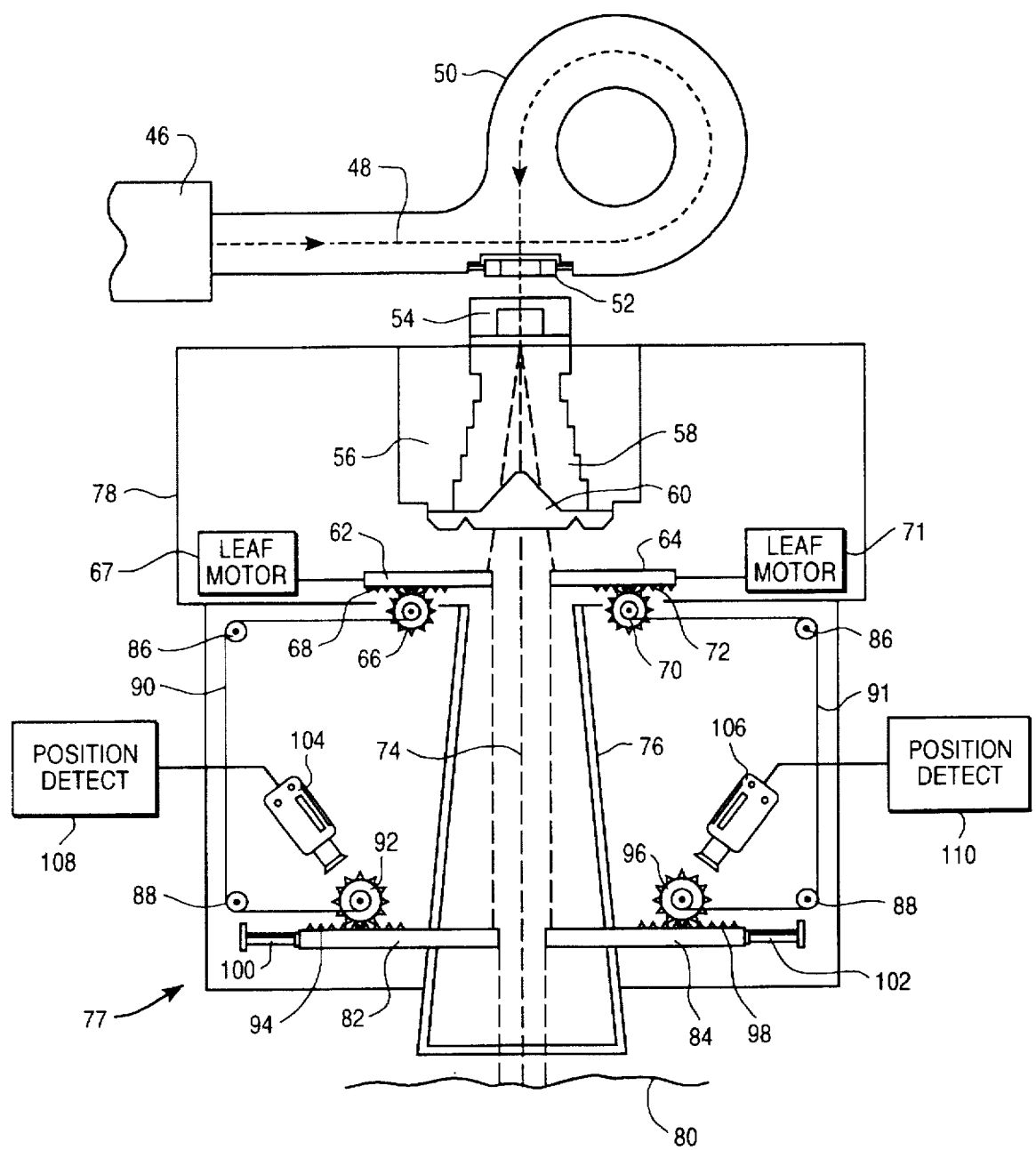
FIG_2

REDUNDANT FIELD-DEFINING ARRAYS FOR A RADIATION SYSTEM

TECHNICAL FIELD

The invention relates generally to systems for applying radiation therapy and more particularly to radiation systems having structures for contouring treatment fields to conform to irregularly shaped regions which are to be treated.

DESCRIPTION OF THE RELATED ART

Radiation-emitting devices are generally known and used, for instance, as radiation therapy devices for the treatment of patients. A radiation therapy device usually includes a gantry which can be swiveled around a horizontal axis of rotation in the course of a therapeutic treatment. A linear accelerator is located in the gantry for generating a high-energy radiation beam for therapy. This high-energy radiation beam can be an electron beam or a photon (X-ray) beam. During treatment, the radiation beam is trained on a zone of a patient lying in the isocenter of the gantry rotation.

An important goal in the treatment of a patient is to minimize exposure of healthy tissue to the radiation beam. Devices that block portions of the emitted beam on a session-by-session basis are utilized to provide varying degrees of conformity between a treatment field and the shape of a region to be treated. Low-scale conformity is achieved using four blocks of material that attenuate radiation. The blocks are contained within a collimator, with two of the blocks being adjustable relative to each other to define an opening in the Y direction and the other two blocks being movable relative to each other to define an opening in the X direction. A disadvantage of such a collimator is that only rectangular treatment fields can be formed. Often, diseased regions, such as a tumor, has an irregular shape. As a result, either the rectangular treatment field must include the exposure of healthy tissue or the field must be limited to expose less than all of the diseased tissue. U.S. Pat. No. 4,220,866 to Taumann et al., which is assigned to the assignee of the present invention, describes a primary collimator for forming rectangular treatment fields. The system of Taumann et al. also includes an electron applicator that is located between the collimator and a patient. The electron applicator includes four L-shaped collimator plates that overlap each other to surround the beam path. The four L-shaped plates can be adjustable either independently or in synchronization with the primary collimator plates. The patent asserts that the electron applicator allows precise adjustment to any symmetric or asymmetric rectangular field-collimation.

A collimator that is better suited for irregularly shaped treatment fields is described in U.S. Pat. No. 5,165,106 to Barthelmes et al., which is assigned to the assignee of the present invention. Two stacks of aperture plates are mounted opposite to each other. The aperture plates are individually moved in order to configure an electron beam. Each stack of aperture plates is mounted on an axle, so that the aperture plates rotate individually around the axle. Alternatively, the aperture plates may move linearly. The collimator of Barthelmes et al. is referred to as a multileaf collimator. By including a sufficient number of aperture plates ("leaves"), irregular shapes can be reliably formed.

The aperture plates of a multileaf collimator are typically separately driven by electrical motors. Moreover, the aperture plates are rotatably mounted and the plates of each stack can be rotated around one axis to define the orientation of the treatment field. Thus, there are a number of known techniques for conforming a radiation beam to a particular region of a patient.

Because of the difference in energy, X-ray beams are "harder" than electron beams. When X-ray beams are used for radiation treatment, the two stacks of aperture plates in the collimator can accurately and reliably deliver radiation to a predetermined region. On the other hand, electron beams are "softer" and tend to migrate outwardly as the stopping power of air causes electron scattering. While X-ray beams are used more often for radiation treatment, certain cancers, such as skin cancer and lung lining cancer, are treated more effectively with electron beams. In order to control electron scatter, electron applicators are utilized. The electron applicator described in Taumann et al. is rectangular and is adjustable. Electron applicators are typically not adjustable. U.S. Pat. No. 4,140,127 to Heinz et al. describes a rectangular electron applicator having fixed limiting apertures that restrict beam migration. Other known electron applicators have interior surfaces that taper inwardly with distance from the collimator. Such an electron applicator is described in U.S. Pat. No. 4,314,158 to Lucido.

While the prior art devices and systems provide protection of healthy tissue from unnecessary exposure to radiation, there are concerns. The electron applicator of Taumann et al. is limited with respect to conforming to a predetermined treatment field. Often, the electron applicators of the types described in Heinz et al. and Lucido include a beam opening that is specifically fabricated to conform to the shape of the field to be treated. Thus, the fabrication must take place on a patient-by-patient basis. This can add significantly to the cost of the treatment plan, particularly if the treatment plan requires exposures of different regions for different sessions.

What is needed is a system for providing radiation therapy of irregular treatment fields, with protection of surrounding tissue in a cost-efficient manner.

SUMMARY OF THE INVENTION

A system for applying radiation therapy includes a multileaf collimator having a first beam-shaping assembly having opposed sets of individually manipulable leaves for defining a contour of a treatment field. The system includes a second beam-shaping assembly adjacent to a patient to be treated. For example, the second beam-shaping assembly may be enclosed within an electron applicator having opposed sets of field-defining members that are individually connected to leaves of the first beam-shaping assembly. Thus, adjusting a position of a leaf simultaneously adjusts a corresponding field-defining member. The second beam-shaping assembly provides a more finely defined treatment field.

In the preferred embodiment, there is a one-to-one correspondence of leaves and field-defining members, with a mechanical linkage of each leaf to its corresponding field-defining member. The mechanical linkage may be selected to establish a desired relationship between travel of a leaf and movement of the corresponding field-defining member. Preferably, the system also includes position encoders, such as sensors that verify the positions of the field-defining members.

BRIEF DESCRIPTION OF THE DRAWINGS

FIG. 1 is a top view of a multileaf collimator in accordance with the prior art.

FIG. 2 is a side view of a system for applying radiation therapy having redundant field-defining arrays in accordance with the invention.

DETAILED DESCRIPTION

With reference to FIG. 1, a multileaf collimator 10 may be used to provide precise delivery of conformal treatment, so that healthy tissue is shielded during the exposure of diseased tissue to radiation therapy. The multileaf collimator includes first and second arrays of leaves that may allow a full treatment field of 40 cm×40 cm, but the dimensions are not critical to the invention. In the embodiment of FIG. 1, the leaves are rotatably mounted, such as those described in U.S. Pat. No. 5,165,106 to Barthelmes et al. However, linearly displaced arrays of leaves are also utilized in the field and may be employed in implementing the invention.

Leaf 12 of the first set of field-defining members is in contact with leaf 14 of the second set of field-defining members. However, the individual leaves of one set may be moved toward and away from aligned leaves of the other set to allow passage of a radiation beam between the aligned leaves. For example, leaf 16 of the first set is spaced apart from the aligned leaf 18 of the second set. The desired spacing between two aligned leaves (i.e., "leaf pair") is determined by the shape of the predefined treatment field. An irregularly shaped treatment field 20 is shown in FIG. 1. The multileaf collimator 10 includes thirteen leaves in each set. Typically, a greater number of leaves are utilized. One conventional multileaf collimator includes twenty-seven pairs of leaves. An increase in the number of leaves increases the preciseness of contouring the treatment field to conform to a target area.

The first and second sets of leaves 14–18 are mounted between rails 22 and 24. For purposes of blocking passage radiation, the pair of leaves 12 and 14 moves in a direction parallel to the rails and in contact with rail 22. In the same manner, a pair of leaves 26 and 28 contacts rail 24. Movement of individual leaves is accomplished by rotating an associated worm gear. Again, the leaf movement may be rotational or linear. Worm gears 30, 32 and 34 are rotated to change the positions of leaves 12, 16 and 26, respectively. Rotations of worm gears 36, 38 and 40 cause displacements of leaves 14, 18 and 28, respectively. Each of the leaves has a worm drive, not shown, that meshes with the spiral groove of the associated worm gear. The worm drives of the leaves may be integrally formed into the leaves or may be formed in brackets that are attached to the leaves.

The worm gears 30–40 are connected to shafts 42 having drive gears 44 at ends opposite to the worm gears. The drive gears are individually connected to a drive mechanism, not shown. In the preferred embodiment, the contour of the treatment field 20 is automatically set. For example, a user may identify a desired shape of a target area, and the implementation of leaf manipulation may be carried out in software. Also in the preferred embodiment, each leaf has a separate motor, so that there is a one-to-one correspondence of leaves to motors. Thus, the drive gears 44 may instead be drive motors that are independently controlled.

While multileaf collimators 10 are known in the art and are used to precisely define a treatment field, the collimators are often sufficiently far from the patient that some beam spreading will occur prior to reaching the patient. Penumbra is a region at the edges of a treatment field that is exposed as a result of phenomena such as scattered radiation. The dose rate along the penumbra changes significantly as a function of distance from the axis of the radiation beam. X-ray beams are "harder" than electron beams. The "softer" electron beams tend to migrate outwardly as the stopping power of air causes electrons to scatter. Referring now to FIG. 2, the effects of beam scattering are controlled or eliminated by a second beam-shaping mechanism.

In FIG. 2, a radiation system for medical applications is shown as including a conventional linear accelerator 46 which generates an electron beam 48 that is accelerated using known energy-transfer techniques. A guide magnet 50 bends the electron beam by approximately 270°. The electron beam then exits through a window 52 that is transparent to the beam, but preserves the vacuum condition within the linear accelerator and guide magnet. The window may be formed of titanium, but this is not critical.

The emitted electron beam may be caused to impinge a target 54 to produce scattering photon radiation. Alternatively, a scattering foil may be used in place of the target. The scattering foil causes the radiation beam to remain as an electron beam, but in a conical form.

The conical radiation beam enters a primary collimator 56 having a stepped interior 58. The primary collimator provides an initial limitation of the expansion of the conical radiation beam. Within the stepped interior is a stainless steel flattening filter 60. The flattening filter has a conical design that is contoured to provide desired beam characteristics, e.g., beam homogeneity.

The conical radiation beam emerges from the primary collimator and reaches a multileaf collimator of the type described with reference to FIG. 1. In the side view of FIG. 2, only one pair of leaves 62 and 64 is shown. Rather than the rotatable leaves of FIG. 1, the leaves 62 and 64 move linearly. However, this is not critical. The aperture between the leaf pair determines the dimension of the portion of the treatment field associated with the pair. Each leaf of a multileaf collimator is formed of a material that blocks passage of the radiation that impinges the leaf.

A pinion gear 66 meshes with teeth of a rack 68 on the underside of the leaf 62. A leaf motor 67 drives the leaf 62 toward and away from leaf 64. Because the pinion gear meshes with the rack 68, lateral movement of the leaf causes rotation of the pinion gear. Clockwise rotation of the pinion gear 66 is initiated when the motor 67 drives the leaf 62 closer to the leaf 64. On the other hand, counterclockwise rotation of the pinion gear is initiated when the space between the two leaves is increased. Linear displacement of the leaf 64 includes similar structure. A leaf motor 71 drives the leaf 64, and a pinion gear 70 which meshes with teeth of a rack 72 on the underside of the leaf 64. Rotation of the pinion gear 70 results from movement of the motor-driven leaf 64 relative to the axis 74 of the radiation beam and relative to the leaf 62.

By adjusting the apertures between the various leaf pairs in a multileaf collimator, the treatment field is defined. However, as previously noted, the radiation beam does not remain well defined when the collimator is at a significant distance from the target, such as a patient. Beam scattering is particularly a concern if the radiation beam is an electron beam. The invention of FIG. 1 includes an elongated conical housing 76 that is adapted to provide a more precise electron beam pattern. In the preferred embodiment, the conical housing provides a beam guide that matches the beam shape and the size of the treatment field that is to be irradiated. The conical housing is a portion of a multi-blade electron applicator 77 that is removably connected to the conventional machine head 78. The electron applicator and its conical housing can be connected or removed according to treatment plans of individual patients. During conventional use, the conical housing is brought into contact with the patient or is spaced apart from the patient by a gap of approximately 5 cm, but the gap will vary according to the clinical application.

Connected to the conical housing 76 are sets of fingers 82 and 84. In the same manner that the leaves 62 and 64 operate as field-defining members for the multileaf collimator, the fingers 82 and 84 are field-defining members immediately adjacent to the surface to be treated, i.e., the patient 80. The fingers are located at the end of the conical housing and are dynamically adjusted to match the collimator pattern of leaves. In the preferred embodiment, there is a one-to-one correspondence between the leaves 62 and 64 and the fingers 82 and 84, but each finger extends closer to the beam axis 74 than its corresponding leaf. For example, the fingers may be 5 cm closer to the beam axis (system isocenter). The leaves achieve primary field-forming and the fingers "trim" the contoured beam to sharply define the desired treatment field at the patient 80. The finger 82 is associated with the leaf 62, while the finger 84 is associated with the leaf 64. A mechanical linkage connects the finger to its associated leaf. In FIG. 2, the mechanical linkage is shown as including a pair of rollers 86 and 88 and a pair of belt-like members 90 and 91. With regard to the finger 82, the dedicated belt-like member 90 is connected to a follower gear 92 that meshes with teeth of a rack 94 on the finger. For the finger 84, the second belt-like member 91 is connected to a second follower gear 96 which meshes with the teeth of a rack 98 on the finger 84.

If the movement of the fingers 82 and 84 relative to the beam axis 74 is to match the beam-shaping capacity of corresponding movement of the leaves 62 and 64, the gear ratio of a motor-driven pinion gear 66 and 70 to a mechanically linked follower gear 92 and 96 must be properly established. The fingers are larger than the leaves, since electron scattering causes the radiation beam to increase in size with approach to the patient. Each finger is formed of a soft material, such as aluminum or similar material, which is capable of blocking the electron beam.

An advantage of the invention is that irregular treatment fields can be patterned in close proximity to the patient 80. While only two fingers 82 and 84 and two leaves 62 and 64 are shown in the side view of FIG. 2, the first and second beam-shaping assemblies include opposed sets of leaves and fingers. For example, each illustrated leaf and each illustrated finger may be the first of twenty-seven field-defining members in a set. Because the fingers establish a desired field pattern close to the patient, healthy tissue is more reliably shielded from exposure that might otherwise occur as a result of beam scattering.

In the preferred embodiment, the mechanical links between the leaves 62 and 64 and the fingers 82 and 84 are easily disconnected, so that the electron applicator 77 is easily removed. Each finger is connected to an end of a spring member 100 and 102. The opposite ends of the spring members are fixed in position. When the mechanical linkage is disengaged, the spring members exert forces to separate the fingers. As a result, the fingers have known rest positions. Providing known rest positions is important in the alignment of the position of a finger to its associated leaf. For example, the reattachment of the mechanical links may be preceded by driving the leaves 62 and 64 to their maximum rearward position, so that all of the leaves and all of the fingers are at their rearward extremes within the range of movement. Consequently, the leaves and fingers will have corresponding start positions.

Position encoders 104 and 106 may be included to verify the positions of the fingers 82 and 84. The position encoders are shown as sensors that generate signals indicating finger position. However, other encoders may be utilized. For example, mechanical encoders may be connected to the individual follower gears 92 and 96. The use of the position encoders provides protection of a patient. The encoders may be used to track the rotation of the follower gears 92 and 96, or may be directed at the fingers 82 and 84, or may be directed at the aperture that is formed by the sets of fingers. Position detector circuits 108 and 110 are utilized to provide the verification prior to initiating radiation treatment.

In the embodiment of FIG. 2, the conical housing 76 increases in diameter with distance from the source of the radiation beam. However, this is not critical. The redundant field-defining arrays may be employed in an embodiment in which the conical housing decreases in diameter with distance from the beam source. U.S. Pat. No. 4,314,158 to Lucido describes a conical electron applicator that decreases in diameter. The fingers 82 and 84 of FIG. 2 may be incorporated into the end of the electron applicator of Lucido. In such an embodiment, the gear ratio of the motor-driven pinion gears 66 and 70 to the follower gears 92 and 96 should be selected to cause the leaves 62 and 64 to move further than the fingers 82 and 84 for a comparable field-pattern adjustment. Because the patient end of the electron applicator is relatively small, only a fine adjustment is needed by the fingers to achieve a desired result. The leaves function as primary trimmers (for collimation), while the fingers function as secondary trimmers.

The redundant field-defining arrays may also be implemented with electron applicators of other shapes. For example, the two arrays of fingers 82 and 84 may be housed within an elongated rectangular device.

The mechanical connection of the fingers 82 and 84 to their associated leaves 62 and 64 is the preferred embodiment. However, each leaf can be connected to a finger electronically. The position of a particular leaf can be electronically determined and then mimicked by the corresponding finger. In another embodiment, the signals for setting up the leaf positions in the multileaf collimator can be directed to drives for manipulating the fingers. The parallel signaling can be implemented in a computer program. Separate drives may be used to independently position the fingers.

Preferably, the fingers 82 and 84 are manipulated automatically. For example, a patient identification number can be obtained and used to identify a treatment plan that is stored in system memory. The treatment plan defines the contour of the treatment field to be irradiated and provides the information for positioning the leaves 62 and 64 and the fingers 82 and 84. Thus, the field-defining arrays are automatically manipulated on a patient-by-patient basis and even on a session-to-session basis for a particular patient.

I claim:
1. A system for applying radiation therapy comprising:
   a radiation source for emitting a radiation beam;
   a multileaf collimator having a first shaping means for defining a contour of a treatment field, said first shaping means having a plurality of leaves, including a first set of side-by-side leaves which are individually manipulable to extend toward and away from a second set of individually manipulable side-by-side leaves;
   a second shaping means for defining said contour of said treatment beam, said second shaping means being on a side of said multileaf collimator opposite to said radiation source, said second shaping means having a third set of field-defining members that are individually connected to corresponding leaves of said first set, said second shaping means having a fourth set of field-defining members that are individually connected to corresponding leaves of said second set; and
   means for adjusting said leaves of said first and second sets to vary said contour of said treatment field, wherein adjusting a position of a leaf simultaneously adjusts a position of a field-defining member connected to said leaf.

2. The system of claim 1 wherein said field-defining members of said third set have a one-to-one correspondence with said leaves of said first set and wherein said field-defining members of said fourth set have a one-to-one correspondence with said leaves of said second set.

3. The system of claim 2 wherein each field-defining member is mechanically linked to a leaf.

4. The system of claim 3 wherein mechanically linking a field-defining member to a leaf includes linking a drive gear connected to said leaf with a follower gear connected to said field-defining member.

5. The system of claim 1 wherein said first and second shaping means are connected to said means for adjusting, a connection of said first shaping means providing a greater displacement of said leaves relative to displacement of said field-defining members when positions of said leaves are adjusted.

6. The system of claim 1 further comprising position encoders responsive to adjustments of said field-defining members.

7. The system of claim 6 wherein said position encoders include sensors for forming video signals indicative of said adjustments.

8. The system of claim 1 wherein said leaves are mounted for linear adjustment by said means for adjusting, said field-defining members being linearly displaceable fingers.

9. The system of claim 1 wherein said second shaping means is housed within a conical member attached to said multileaf collimator.

10. A system for applying radiation therapy comprising:

a radiation source for directing a radiation beam along a beam path;

a contour collimator positioned along said beam path, said collimator having first and second arrays of closely proximate coarse field-defining members, each coarse field-defining member of said first array being operatively associated with a coarse field-defining member of said second array, said operatively associated coarse field-defining members being displaceable to selectively vary a first beam passageway therebetween;

an applicator connected to said contour collimator along said beam path, said applicator having third and fourth arrays of closely proximate fine field-defining members, each fine field-defining member of said third array being operatively associated with a fine field-defining member of said fourth array, said operatively associated fine field-defining members being displaceable to selectively vary a second beam passageway therebetween, said fine field-defining members being movable in a direction generally coincident with movement of said coarse field-defining members; and mechanical linkage connecting each of said coarse field-defining members with one of said fine field-defining members to establish a one-to-one correspondence with respect to displacement of said coarse and fine field-defining members.

11. The system of claim 10 wherein said mechanical linkage includes first and second gears having a gear ratio such that displacement of a coarse field-defining member is less than displacement of a fine field-defining member connected to said coarse field-defining member by said mechanical linkage.

12. The system of claim 10 wherein said applicator has a truncated conical shape having a diameter that increases with distance from said collimator.

13. The system of claim 10 further comprising position encoders disposed relative to said fine field-defining members to be responsive to adjustments of said fine field-defining members.

14. The system of claim 10 further comprising drive means for selectively displacing said coarse field-defining members, thereby displacing said fine field-defining members.

15. The system of claim 14 further comprising processing circuitry for automatically controlling said drive means based upon identification of a patient to be treated.

16. The system of claim 10 wherein said coarse field-defining members are collimator leaves and wherein said fine field-defining members are applicator fingers.

* * * * *